(12) United States Patent
Kyriakopoulos

(10) Patent No.: US 10,772,855 B2
(45) Date of Patent: Sep. 15, 2020

(54) N-BROMOTAURINE SOLUTIONS AND EMULSIONS AGAINST ABNORMAL CELLS

(71) Applicant: NASCO AD BIOTECHNOLOGY LABORATORY, Pireus (GR)

(72) Inventor: Antonios Kyriakopoulos, Pireus (GR)

( * ) Notice: Subject to any disclaimer, the term of this patent is extended or adjusted under 35 U.S.C. 154(b) by 72 days.

(21) Appl. No.: 16/079,997

(22) PCT Filed: Feb. 17, 2017

(86) PCT No.: PCT/GR2017/000007
§ 371 (c)(1),
(2) Date: Aug. 25, 2018

(87) PCT Pub. No.: WO2017/149331
PCT Pub. Date: Sep. 8, 2017

(65) Prior Publication Data
US 2019/0060260 A1    Feb. 28, 2019

(30) Foreign Application Priority Data

Mar. 1, 2016 (GR) .............................. 20160100072

(51) Int. Cl.
| | | |
|---|---|---|
| *A61K 31/185* | (2006.01) | |
| *A61K 9/00* | (2006.01) | |
| *A61K 47/36* | (2006.01) | |
| *A61K 47/44* | (2017.01) | |
| *A61K 9/06* | (2006.01) | |
| *A61K 9/08* | (2006.01) | |
| *A61K 9/107* | (2006.01) | |
| *A61K 9/70* | (2006.01) | |
| *A61P 17/00* | (2006.01) | |
| *A61P 31/22* | (2006.01) | |
| *A61P 17/06* | (2006.01) | |

(52) U.S. Cl.
CPC .......... *A61K 31/185* (2013.01); *A61K 9/0014* (2013.01); *A61K 9/06* (2013.01); *A61K 9/08* (2013.01); *A61K 9/107* (2013.01); *A61K 47/36* (2013.01); *A61K 47/44* (2013.01); *A61P 17/00* (2018.01); *A61P 17/06* (2018.01); *A61P 31/22* (2018.01)

(58) Field of Classification Search
CPC .......... A61P 31/12; A61P 31/14; A61P 31/20; A61P 31/22; A61K 31/185; A61K 2300/00; A61K 9/107
See application file for complete search history.

(56) References Cited

U.S. PATENT DOCUMENTS

2004/0214891 A1* 10/2004 Marcinkiewicz ....... A61P 17/10
514/553

* cited by examiner

*Primary Examiner* — Kortney L. Klinkel
(74) *Attorney, Agent, or Firm* — James O. Zigouris

(57) ABSTRACT

In a method of producing aqueous solutions of N-bromotaurine (Taurine Bromanine, NBrT) with taurine with latter addition of NaOBr, and emulsions of these solutions with Stable Produced Olive Oil (S.P.O.O.), so to use against hyper-proliferative and abnormally differentiating cells of human and mammalian origin. In addition, due to the hyper-proliferation of keratinocytes in psoriatic skin, the methodology and subsequent use of the aqueous solutions and emulsions derived from this invention, containing NBrT and taurine, and S.P.O.O. against the lesions of psoriasis. With the method of this invention, the solutions derived and applied on cells in vitro beneficially provide maximization of NBrT anti-proliferative properties on abnormally differentiating and hyper-proliferating cells of human and mammalian origin by restoring NBrT anti-proliferative activity in a solution, whilst leaving unaffected the proliferation of normally dividing human fibroblasts. The use of NBrT/taurine solutions in psoriasis optimally comprises the simultaneous use of S.P.O.O. by concurrent mixing to make an emulsion. S.P.O.O. is derived from a patented physical refinement of olive oil [GR 1008334(B)] and is mixed with N-bromotaurine/taurine solutions to produce an active emulsion, and thereafter to derive ointments, creams, lotions, as medicinal preparations to treat psoriasis and Herpes Zoster dermatoses. Beneficially, when S.P.O.O. is utilized to make an emulsion with NBrT/taurine aqueous solutions and applied on psoriatic lesions coupled with NaOBr latter addition this shortens to half the time period for psoriasis lesions regression and minimizes side effects on dermal tissue as compared to the NBrT aqueous solution application on psoriatic lesions.

17 Claims, 1 Drawing Sheet

| Cell line | Percentage (%) of decrease in proliferation at 24/48/72 hours of incubation of cancer cell lines with the methodology of this invention (NBrT / taurine solutions) where 1 % of NaOBr to the concentration of NBrT is added at 24/72/48 hours of incubation in comparison (relation) with the aqueous solutions of NBrT without surplus of taurine and without later addition of NaOBr | | |
| --- | --- | --- | --- |
| | 62.5μM NBrT & 312.5 μM Taurine at 24/48/72 hours | 125μM NBrT & 625μM Taurine at 24/48/72 hours | 250μM NBrT & 1250μM Taurine at 24/48/72 hours |
| HLF-1 (Normal fibroblast – control) | 0/0/0 | 0/0/0 | 0/0/0 |
| PC3 (Prostate cancer) | 3/4/5 | 12/24/53 | 23/35/62 |
| HeLa (Cervical cancer) | 1/3/10 | 5/11/18 | 23/48/90 |
| HepG2 (Hepatocellular cancer) | 2/8/12 | 5/19/33 | 28/43/83 |
| MD-MB-231 (Breast cancer) | 10/17/25 | 25/40/65 | 32/54/82 |
| A549 (Lung cancer) | 2/5/10 | 10/25/45 | 23/42/78 |

N-BROMOTAURINE SOLUTIONS AND EMULSIONS AGAINST ABNORMAL CELLS

The present invention relates generally to the method of producing aqueous solutions of N-bromotaurine (Taurine Bromamine, NBrT) with a surplus of Taurine and their subsequent emulsions with the Stable Olive Oil produced Through filtration by Cellulose Membrane (S.P.O.O., GR 1008334(B)][1], as well as their use against hyper-proliferating and abnormally differentiating cells, including cancer cells and in the materials for the topical treatment of Psoriasis. Specifically the invention relates to the production of aqueous solutions of NBrT with the scope to accelerate its anti-proliferative activity against hyper-proliferating human and mammalian cells, and also accelerate psoriasis lesion regression whilst minimizing side effects on normally proliferating cells and dermal tissue.

Specifically this invention relates to a) the construction of appropriate solutions that correct the lack of NBrT stability and increase its efficiency against hyper-proliferating cells such as cancer cells, and b) the emulsions that derive from the mixture of the NBrT/taurine aqueous solutions of the present invention with the S.P.O.O. that when applied topically onto psoriatic lesions result to the decrease of time period for these lesion to regress and to the decrease of side effects noticed with aqueous solutions of NBrT on the dermis tissue during treatment. These resulting emulsions of NBrT/taurine aqueous solutions with S.P.O.O form the basis of cosmetic and pharmaceutical products so to be used on materials and methods for the topical treatment of psoriasis.

BRIEF DESCRIPTION OF THE DRAWINGS

A FIGURE illustrates a percentage decrease in proliferation at 24/48/72 hours of incubation of cancer cell lines.

Psoriasis is a common chronic multi-systemic autoimmune disease with various phenotypes located a) on the skin as general, localized, palmoplantar, facial scalp genital and nail, and b) the joints. Severity is distinguished by the extent of body surface involved, the clinical presentation of lesions, and the involvement of joints presenting psoriatic arthritis. On the skin, scaling erythema, and thick plaques are due to abnormal differentiation and hyperproliferation of epidermal keratinocytes and a dysfunction of interplay of the immune system on the dermal/epidermal junction and the microvascularisation system of the skin. Pathogenesis of the disease is mainly attributed to wrong communication between Th1 and Th17 subsets of T cells, secreting over amounts of Inteleukin (IL) 17 and IL 22, thus promoting the proliferation of keratinocytes and the stimulation of cytokine derived cytokines and chemokines that recruit more and more immune cells at the site of auto-inflammation. Central and initial to this inflammatory reaction is the chemoattraction of neutrophils which are the first to be recruited to the site of a disease tissue. Neutrophils are the first cells to appear on initial stages of psoriasis. Psoriatic patients have increased numbers of circulating neutrophils with those of psoriatic arthritis (a latter disease stage), having the greatest numbers. The activated neutrophils generate a variety of reactive oxygen species (ROS) that may attribute to pathogenic effects of psoriatic tissue[2]. The central IL 17 contribution to psoriasis pathogenesis and the development of psoriatic arthritis is similar to the pathogenesis of rheumatoid arthritis in the human and mouse model, and the IL 22 contribution plays an important role not only to the development of autoimmunity but also to the immunity of cancer[19].

Treatment of psoriasis is directed from the state of severity of disease and is categorized to topical and systemic approaches[2]. Topical treatment (often called a first line treatment) involves amongst many others, corticosteroids, calcipotriene/calcitriol (a synthetic derivative of vitamin D), retinoids (synthetic derivatives of vitamin A such as tazarotene), calcineurin inhibitors, and topical phototherapy (UVA and UVB) for limited and resistant plaques. Often there is more than one agent involved in the treatment as a combination therapy is used. Systemic therapy involves various inhibitors of the immune system, such as methotrexate and cyclosporine, monoclonal antibodies against IL 17 T cells such as sucukinomab, acitretin, alefacept, MTX and biologic agents such as TNF blockers, interleukin antagonists and inhibitors. However systemic agents are highly potent against patient's health and maintenance of organism's homeostasis[2].

Taurine is called as a "non essential" amino-acid. Is synthesized from cysteine and although is not incorporated in proteins it is the most abundant amino-acid encountered in organs throughout the body. It is in general a serious component of homeostatic mechanisms presenting various functions, from cell volume regulation by being an organic osmolyte, cytoptotective and developmental factor to modulating intracellular free calcium concentration[3]. Although taurine's biological functions are not fully unraveled, due to the numerous functional properties taurine is considered as one of the most essential substances of the body. Studies indicate that taurine plays a significant role in overcoming insulin resistance and diabetes I and II as its depletion from the organism leads to a wide range of pathological conditions including cardiomyopathy, renal dysfunction, pancreatic β-cell dysfunction, and the loss of retinal photoreceptors. Taurine's role against inflammatory diseases becomes increasingly important for Biomedical Sciences[4].

N-Bromotaurine (NBrT) is one of the major endogenous haloamines that is generated from taurine at the site of inflammation by neutrophil and eosinophil myeloperoxidase system through a cascade of oxidizing reactions. It is part of the innate immune system that has increased antimicrobial properties, sometimes with damaging abilities to the host tissue, but also possessing potential anti-inflammatory properties[5,16]. NBrT works on the inactivation of ROS and $H_2O_2$ produced by activated leukocytes and together with the induction of Heme oxygenase gene has a role of immune regulation and anti-oxidant capacity to attenuate oxidative stress[6]. Patent EP 1663195 A2 and thereafter WO2004093583A2, is a method for inhibiting pathogenic bacteria and fungi in a solution of various concentrations with NBrT[7]. NBrT has also been shown to inhibit IL6 and inflammatory mediators ($PEG_2$), on a cellular in vitro model of fibroblast-like synoviocytes that participate in rheumatoid arthritis[6].

S NBrT is claimed to be beneficial for acne treatment (EP 1663195 A2) by inhibiting bacterial growth of *Propionibacterium acnes, Staphylococci* spp. and fungi responsible for acne pathogenesis. Contribution to the anti-inflammatory activity and its role in immunity of NBrT is described by means of inhibiting bacterial and fungal growth and its anti-oxidant activity[7]. NBrT can be synthesized using various biochemical methods[6]. Biochemical method of NBrT synthesis described in EP 1663195 A2 patent (WO 2004093853 A3), results in the generation of N-Bromotaurine (Taurine bromamine, NBrT) in aqueous solutions[7]. However, with this methodology, significant variation of decreasing concentration of NBrT as observed by decreasing absorbance values that reflect to decreased biological activities of NBrT aqueous solutions are recorded. Disintegration reactions occur in the chemical structure of a very close relative (chemically), the haloamine Taurine Chloramine (N-Chlorotaurine, TauCl, NCT), to the NBrT structure. TauCl structure is disintegrated by the release of HCl at room temperature, although a retardation of decomposition is achieved at 2-4° C. and is slower as compared to other N-chloro-derivatives as the α-amino-carbonic acids[8]. Other subsequent degradation and transformation events of TauCl structure which result to β-aminosulphonic acid, are spontaneous hydrolysis to yield an aldehyde and ammonia[8]. In the case of NBrT, the bromide atom as a halogen is heavier than chloride atom having a greater atomic number, and thus is more readily decomposed from NBrT structure when attached to the amino group, as compared to the chloride atom in the TauCl structure. The bromide atom reacts with $H^+$ and produces spontaneously $H^+Br^-$ in an aqueous solution. This series of events result to rapid disintegration of NBrT molecule when present in an aqueous solution.

The use of NBrT is described in a pilot clinical study against the microbial load that contributes to the pathogenesis of acne vulgaris[17]. In this study a concentration of NBrT up to 5 mM was applied onto the skin of patients with literally no side effect. Complementary to another clinical study of phase II grade, the close relative compound: N-clorotaurine, (TauCl, NCT), had significant results against purulent leg ulcers. In this study[18], NCT showed increased tolerability, low toxicity when applied locally onto patient's wounds. Complementary in a yet recent case study of a patient suffering from multiple sclerosis that had Herpes Zoster resistant to standard acyclovir treatment, the topical treatment with NCT and NBrT aqueous solutions in synergy provided the appropriate treatment in a very short period of time[21] for the reluctance of patient.

Amongst plant fruit and seed derived oils; Extra Virgin Olive Oil (EVOO) is a mixture of natural derived chemicals that correspond to nutritional and pharmaceutical properties that make it unique. In a real sense it constitutes a miracle mixture of omega monounsaturated (MUFA's) and polyunsaturated fatty acids (PUFA's), phenolic and stanolic antioxidant molecules of ever increasing medicinal properties[10]. The Stable Produced Olive Oil (SPOO) Production Through Filtration by a Cellulose Membrane, GR10083348[2], is a method for producing Olive Oil preparation presenting stable fatty acids concentrations some of which exhibit increasing tendencies for a prolonged time (4 years), without affecting basic chemical characteristics of initial EVOO. Preservation of biological value of EVOO makes it ideal for health application purposes. However in the patent GR1008334B, none of its use of the final product produced by the method of this invention is claimed.

This present invention relates to the method of producing aqueous solutions of NBrT with taurine and their subsequent emulsions with Stable Produced Olive Oil (S.P.O.O.) The aqueous solutions of NBrT of this current invention exert beyond and much greater the anti-proliferative activity against hyper-proliferating and abnormally differentiating cells such as cancer cells, whilst being non-active against normally proliferating cells. The comparison of the maximization of the anti-proliferative activity of NBrT solutions with taurine produced with the method of this invention is made with the aqueous solutions that are described in the invention EP 1663195 A2 (WO 2004093853A2)[7] and in the publication Olszanechi R, Kurnyta M et al 2008[6]. Complementary the emulsions of NBrT with taurine produced by mixing with the S.P.O.O. are beneficial for skin application on psoriasis by means of minimizing side effects encountered by NBrT aqueous solutions described in EP 1663195 A2.

In this present invention the biochemical method that aqueous solutions of NBrT with taurine are made is as follows: 100 ml of 80 mM NBrT are produced by making first a solution of 100 ml 1600 mM Taurine or 20% of the taurine content by weight (taurine: AppliChem, panreac, Germany), secondly 100 ml of 160 mM NaOCl (Sigma Aldrich Germany) in phosphate buffered saline (PBS, Sigma Aldrich Germany), pH 7.2, and thirdly 100 ml 160 mM NaBr pH 10 titrated with NaOH (Sigma Aldrich, Germany). 100 ml of the 160 mM NaOCl are mixed with 100 ml of 160 mM NaBr pH 10, thus producing 200 ml of 80 mM NaOBr. 100 ml of 80 mM NaOBr solution are mixed gradually with 100 ml of 1600 mM Taurine solution. In this way 80 mM of NBrT solution is manufactured leaving the rest of 800 mM of Taurine theoretically not reacting with NaOBr. The final concentration of taurine in the resulting solution is 400 mM due to the final 1:1 dilution. The produced NBrT concentration in molarity was assessed at measuring the extinction coefficient at a wavelength $\lambda_{max}$=286 nm, where the 10 mM of NBrT in solution equals to the value of extinction coefficient with a peak at $430M^{-1} cm^{+1}$ (absorbance)[6].

Stable Produced Olive Oil (S.P.O.O.) was prepared using an initial extra virgin olive oil and a filtering procedure through a filter membrane of 100% cellulose, weight 60 g/m², size of pores 18-20 μm, with a rate of filtration 4 sec/100 ml of water, 0.1% ash, thickness 20 mm and wet bursting strength: > or equal to 40 kPa as main characteristics. The resulted S.P.O.O. produced has principal chemical characteristics: K270=0.10, K232=1.69, ΔK=−0.002, acidity=0.30, hyperoxide value=15.7.

N-bromotaurine (NBrT) emulsions were prepared by diluting 16 mM of NBrT in double distilled sterile water of phosphate buffered saline in an analogy of 1:1 to SPOO and steered adequately to make an emulsion at temperature not exceeding 30° C.

Complementary, the present invention relates to the use of the mixture/emulsions of the produced aqueous solutions of NBrT with taurine, with the S.P.O.O. to produce active emulsions against hyper-proliferative cells such as at the lesions of psoriasis. The use of the aqueous solutions of NBrT of this invention is extended in vivo to the disease of psoriasis that has as a corner stone the hyper-proliferation of keratinocytes[2]. Relevant abnormal differentiation of the epidermal cell layers is noticed also in Herpes Zoster (disease of the skin cause by Herpes virus VZV infection)[20], hence the application of the emulsions deriving from NBr/taurine solutions and S.P.O.O can be extended to this disease.

With the solutions of NBrT/taurine of this present. invention the regression of the lesions of psoriasis: plaques, fistules, papules, hyperkeratinisation, erythema and all others, is achieved in much less time period in comparison to the aqueous solutions resulting from the invention EP 1663195 A2 (WO 2004093853A2)[7] and described in Olszanechi R, Kurnyta M et al 2008[6], Complementary the resulting emulsions of NBrT/taurine solutions of this invention with S.P.O.O. shorten more the time period for psoriatic lesion regression whilst narrowing side effects seen with the solutions of NBrT alone.

The phenotypes of psoriasis that relate to the use of the aqueous solutions of NBrT/taurine of this invention and their subsequent emulsions with S.P.O.O are: plaque, guttate, pustular and erythrodermic on all body skin surface areas: facial-scalp, hands feet and nails, genital and skin folds in all kinds of psoriasis: localized or general psoriasis involving joints.

NBrT is used optimally at concentrations varying from 1-10% content by weight corresponding to 8-80 mM at molarity. This is in accordance to the use of 12.5-40 μM use of NBrT to treat hyper-proliferating and irregularly differentiating cells such as cancer cells in vitro. Specifically, the present invention method consists of the use of NBrT as an essential component to treat psoriatic lesions in the forms of: 1) aqueous solutions a) double distilled sterile water, b) 0.9% NaCl water for injection or c) phosphate buffer saline pH 7.2-7.4, of concentrations 1-100% content by weight of NBrT or 2) the mixture in an analogy 1:1 with the S.P.O.O., which is the final product, oil result, of the patent GR1008334B methodology, to obtain 1-100% TauBr concentration by weight, by making an emulsion.

To overcome structural disintegration events of NBrT in an aqueous solution that were noticed as the loss of the biological activity against hyper-proliferative cells, a method of NBrT preparation as a novel method is described in this invention. With this method NBrT maintains and enhances anti-proliferative activity against hyper-proliferating and abnormally differentiating cell lines whilst causing no effect on normally proliferating and differentiating cell lines. In the already described biochemical method of EP 1663195 A2 patent, NBrT is made by adding NaOBr solution to taurine solution in an analogy of 1 to 10 in concentration. That is to synthesize for example 40 mM NBrT in a solution, equal volume 40 mM of NaOBr need to be added to an equal volume of 400 mM of taurine solution. With the method of EP 1663195 A2 patent to produce NBrT the immediate biochemical disintegration of NBrT is noticed indirectly from the loss of absorbance (UV spectrum at $\lambda$=286 nm, 430 $M^{-1}$ $cm^{-1}$) were the peak corresponds to 10 mM of NBrT in a solution. Also very importantly, this loss of absorbance and hence concentration of NBrT, corresponds to the loss of biological anti-proliferative activity against abnormally differentiating hyper-proliferative cancer cells.

In this current invention, having sound results from proliferation assays[11] of cancer cell lines where the anti-proliferative ability of NBrT against the hyper-proliferative cells: PC3 (prostate cancer cell line), HeLa (cervical cancer cell line), MDA-MB 231 (Breast adenocancinoma cell line), HepG2 (hepatocellular cancer cell line), and A549 (lung cancer cell line) is well recorded, in order to obtain enhancement of NBrT anti-proliferative properties in time, the NaOBr solution is added at half the concentration required to react with the whole of taurine present in a solution. That is for 100 ml of 800 mM Taurine solution, or 10% content by weight in sterile double distilled water, 100 ml of 40 mM NaOBr (by mixture of equal amounts in volumes of 40 mM NaBr pH 10, and 40 mM NaOCl) are added to the taurine solution, in this way, the initial concentration of 400 mM of taurine but now diluted to 200 mM, remains as a surplus in a 40 mM NBrT final solution. With this method of producing NBrT aqueous solutions a maximization of anti-proliferative effect with time duration of solution storage at 4° C. against cancer cells is achieved.

The same accounts by later addition of Taurine to a 200 mM concentration in a 40 mM NBrT solution to cause enhancement of anti-proliferative effect against cancer cells. The enhancement of anti-proliferative effect against cancer cells is achieved by the use of the surplus of taurine present in the solution that is thereafter reacting with a later addition of 40 μM NaOBr solution at 24, 48 and 72 hours of in vitro incubation of cancer cells. That is, with a 1% addition of 40 μM NaOBr solution in total volume of cell cultures at 24, 48 and 72 hours, i.e. 0.4 μM NaOBr, favorable circumstances for fresh NBrT synthesis are made in order to contribute to reaction against abnormally hyper-proliferative cells. This results to an accelerating anti-proliferative effect on all hyper-proliferating cell lines tested: A549, PC3, HeLa MDA-MB 231, and HePG2, and literally no effect on normally proliferating fibroblast cell line HFL-1 at NBrT concentration range of 12.5-40 μM. Normally proliferating cell lines show an evident decrease in their proliferative ability when grown at concentrations of NBrT above 250 μM. It has to be noted that all cells tested are not affected in their proliferation rate when growing in the same medium containing 0.4-40 μM NaOBr. In general, in order to achieve acceleration of anti-proliferative effect on hyper-proliferating cells without causing damage on proliferation of normal cells the concentration of NBrT in solution is 1:5 the concentration of estimated Taurine and the addition of NaOBr solution at latter stages of treatment is 1:100 the concentration of NBrT and 1:500 the concentration of Taurine.

It is well known that taurine molecule is much more stable in structure than the derivative molecule, NBrT[8]. As mentioned the lack of stability of NBrT in aqueous solutions was observed and tightly connected with the loss of anti-proliferative effect against cancer cell experiments during studies that have led to this invention.

During studies on NBrT anti-proliferative effect against cancer cells, aqueous solutions of NBrT in double distilled water or phosphate buffered saline where left for 15, 30 and 45 days in room temperature or at 4° C. The anti-proliferative effect of NBrT solutions was decreased by 30-40% each time a respective solution was tested that was left for 15, 30 or 45 days since time of production in comparison with the results of the anti-proliferative effect obtained from the same but fresh solution of NBrT, tested at the same day of production. The same results were noticed in all cancer cell lines tested (A549, PC3, MDA-MB 231, HeLa, and HepG2).

The loss of anti-proliferative effect of the aqueous solutions of NBrT (15, 30, 45 days) was tightly connected with the loss of corresponding absorbance at 286 nm having as a reference that a solution of 10 mM NBrT has a peak at $430 M^{-1}$ $cm^{-1}$ at day of production.

The basic element of the aqueous solutions of NBrT of this invention is that they also contain taurine. Taurine remains as surplus in solution since the overall initial concentration of taurine has remained not reacted with adequate amount of NaOBr. For example, in 100 ml of 800 mM taurine solution or about 10% concentration per weight (125.15 g/mol=1M), in either distilled water or in phosphate buffered saline (pH 7.2-7.4), 100 ml of 40 mM NaOBr solution are added. In this way, 40 mM of NBrT are made, and 400 mM of taurine remain not reacted but as a surplus in solution since the overall concentration of taurine has not been modified biochemically to produce NBrT. The final concentration of taurine in resulting solution is 200 mM post addition of two the equal volume solutions. Therefore the final concentrations of NBrT/taurine in the resulting solution of this invention are 40 mM NBrT/200 mM taurine. The same could be reached if taurine is added latter in a concentration of 200 mM in a solution where 40 mM are synthesized without having remaining taurine as a surplus. However, the enhancement of anti-proliferative effect against cancer cells is achieved by the use of the surplus of taurine present in the solution that is then reacted with a later addition of 40 μM NaOBr solution at 24, 48 and 72 hours of in vitro incubation of cancer cells. That is for a 1% addition of 40 μM NaOBr solution in total volume of cell cultures at 24, 48 and 72 hours, i.e. 0.4 μM NaOBr, favorable circumstances for fresh NBrT to be produced, are made, in order to react with abnormally differentiating and hyper-proliferative cells such as cancer cells.

The methodology of this invention with NBrT/taurine results to an accelerating anti-proliferative effect on all hyper-proliferating cell lines tested: A549, PC3, HeLa MDA-MB 231, and HePG2, having literally no effect on normally proliferating fibroblast cell line HFL-1.

The methodology of this invention with the particular solutions of NBrT/taurine in α concentration range that produce cytotoxicity to cancer cells: from 12.5 μM NBrT/ 62.5 μM taurine to 250 μM NBrT/1250 μM taurine, shows no effect on normally proliferating cell lines such as HLF-1. This particular cell line shows an evident decrease in cellular proliferative ability when grown at concentrations of NBrT above 250 μM/1250 μM taurine.

It has to be noted again that all cells tested are not affected in their proliferation rate when growing in the same medium containing 0.4-4 μM NaOBr. In general, in order to achieve acceleration of anti-proliferative effect on hyper-proliferating cells without causing damage on proliferation of normal cells the NBrT concentration in solution should be 1:5 the concentration of estimated Taurine and the addition of NaOBr solution at latter stages of treatment is 1:100 the concentration of NBrT and 1:500 the concentration of Taurine.

Following, a more detailed description of the enhancement of the anti-proliferative effect obtained with the methodology of this invention, having the aqueous solutions of NBrT/taurine, is given. Stock solution of 4 mM NBrT/20 mM taurine was diluted in final concentrations of 62.5, 125, 250 μM NBrT and 312.5, 625, 1250 μM taurine, respectively, in culture medium DMEM/10% FBS.

During cell cultivation NaOBr solutions of 62.5 mM, 125 mM and 250 mM were added in 1:100 dilution to the corresponded 62.5, 125, and 250 μM NBrT and 312.5, 625, 1250 μM taurine every 24/48/72 hours. The calculation of the increase of anti-proliferative activity in cancer cells with the methodology of this invention was made in comparison to the rate of anti-proliferative effect that solutions of NBrT exert in final concentrations of 62.5, 125 and 250 μM in the same cultivation medium. The effect of NBrT/taurine solutions with latter addition of NaOBr, namely the solutions of this present invention were compared with effect obtained by NBrT solutions without a surplus of Taurine and without latter addition of NaOBr using the same cell lines in the same experiment. Also, it was also confirmed that a surplus of Taurine or latter addition of NaOBr in NBrT solutions as single parameters, do not exert any enhancement of anti-proliferative effect against these cancer cells. The anti-proliferative effect on all cell cultures was measured as a means of cellular viability by Optical Density at 595 nm using a Tecan reader using a crystal violet reagent. All experiments were performed in triplicate and mean values were used.

Percentage (%) of decrease in proliferation at 24/48/72 hours of incubation of cancer cell lines with the methodology of this invention (NBrT/taurine solutions) where 1% of NaOBr to the concentration of NBrT is added at 24/72/48 hours of incubation in comparison (relation) with the aqueous solutions of NBrT without surplus of taurine and without later addition of NaOBr

| Cell line | 62.5 μM NBrT & 312.5 μM Taurine at 24/48/72 hours | 125 μM NBrT & 625 μM Taurine at 24/48/72 hours | 250 μM NBrT & 1250 μM Taurine at 24/48/72 hours |
|---|---|---|---|
| HLF-1 (Normal fibroblast - control) | 0/0/0 | 0/0/0 | 0/0/0 |
| PC3 (Prostate cancer) | 3/4/5 | 12/24/53 | 23/35/62 |
| HeLa (Cervical cancer) | 1/3/10 | 5/11/18 | 23/48/90 |
| HepG2 (Hepatocellular cancer) | 2/8/12 | 5/19/33 | 28/43/83 |
| MD-MB-231 (Breast cancer) | 10/17/25 | 25/40/65 | 32/54/82 |
| A549 (Lung cancer) | 2/5/10 | 10/25/45 | 23/42/78 |

Hereby, it has to be noted again that the surplus of taurine in solution as well as the addition of NaOBr in solutions of NBrT in concentration range: 62.5-250 μM, as single experimental parameters do not confer enhancement of anti-proliferative activity against the cancer cells tested. With the particular methodology of this invention, the combination of all parameters: a) solutions of NBrT of concentration range 62.5-250 μM, with b) presence of taurine in concentration range 312.5-1250 μM respectively, and with c) addition every 24 hours in 1:100 dilution of NaOBr solutions of concentration range 62.5-250 μM, i.e. 0.625-25 μM respectively in cultivation media, all these parameters together, lead to the cancer cell percentage decrease of proliferation rate as presented above and in comparison to the anti-proliferative effect recorded by NBrT aqueous solutions of concentration range: 62.5-250 μM with the same cancer cell lines cultivated in the same culture medium without surplus of taurine and latter addition of NaOBr.

Since hyper-proliferation of keratinocytes is central to psoriasis pathogenesis[2,] the methodology of this current invention against hyper-proliferative cancer cells, that is the final aqueous solutions of NBrT that have a surplus of not reacted taurine present and thereafter sustaining the addition of analogous solutions of NaOBr in dilution 1:100 of the concentration of NBrT and 1:500 the concentration of taurine present, that lead to increase of anti-proliferative activity against cancer cells, was applied to a volunteer with plaque psoriasis. The NBrT/taurine aqueous solutions used had 8 mM NBrT/40 mM taurine in sterile double distilled water and the NaOBr solution used separately was 0.08 mM. The application was straight onto the psoriatic lesions by spraying 4-6 puffs (130 μl each puff), twice a day with the solution of NBrT/taurine, and once a day after 24 hours with the solution of NaOBr. In this period the volunteer had a complete regression of plaques on both knees and elbows. The tolerable side effects were encountered at the first 40 days of application. These were mild itching, erythema, burning sensation and bleeding episodes due to overstretched fragile skin.

The anti-inflammatory activity of NBrT has been shown in the study of Olszanechi R et at 2008, were it was found that there was an inhibition of Prostaglandin $E_2$ production (eicosanoid $PGE_2$) via the genome of Heme Oxygenase[6] by NBrT. The eicosanoids including the prostaglandins and the leucotrienes have a central role in the induction of inflammation and cancer[12]. These eicosanoids are products of the arachidonic acid metabolism via enzyme reactions of lipoxygenase and cycloxygenase[13].

The Stable Produced Olive Oil (S.P.O.O) conserves stable the contained arachidonic acid concentration within the Olive Oil mixture of fatty acids (even for 4 years post production) letting to suggest that as a natural product does not involve enzymatic activity from secondary lipoxygenase subunits due to their gene transcripts remains in olive oil[14]. Also the Omega fatty acid concentrations remain stable and are relatively enhanced over time.

In this invention, in order to optimize NBrT use on psoriatic dermal tissue, an emulsion has produced as resulting from mixing of NBrT/taurine aqueous solutions with S.P.O.O. The emulsion results from the vigorous mixing of 16 mM NBrT and 80 mM taurine in double distilled water with equal volume of S.P.O.O. at 25-30° C. The application of this emulsion in yet another volunteer with plaque psoriasis with equal severity and extent of psoriatic lesions [as defined by the test: Psoriasis Weighted Extend and Severity Index—(P.W.E.S.I) test][15], proved that the use of this emulsion by spraying straight onto psoriatic lesions 6-8 puffs (130 µl each puff), two times a day for 30 days together with application of 0.08 mM NaOBr solution (1 times a day for 30 days), led to complete regression of psoriatic lesions of equal severity and extent in half the time needed by applying only the aqueous solutions of 8 mM NBT and 40 mM taurine (in combination with 0.08 mM NaOBr solution sprayed once a day). Moreover, the application of the emulsion of this invention has the advantage of almost complete alleviation of side effects (itching, burning sensation, erythema and bleeding) noticed by NBrT 8 mM/40 mM taurine aqueous solutions application onto psoriatic lesions.

The emulsion and the methodology of this invention can be used in all phenotypes of psoriasis, such as plaque, pustular, erythrodermic and others. Also the emulsions can be used in cases of; 1) Extended (general) psoriasis, 2) local psoriasis, 3) facial scalp psoriasis, 4) palmoplantar (hands and feet) 5) Genital-anal areas. The application can be achieved by spraying locally the affected areas (6-8 puffs, 130 µl of each puff) are adequate to cover the lower part of the leg of a patient with severe plaque psoriasis.

The emulsion of this invention can form the basis of cosmetic and pharmaceutical grade products to be used as materials for the treatment of psoriasis.

For stabilization of phase separation of emulsion (although stable produced olive oil poses greater hydrophilic properties than initial olive oil) optimally xantan gum is used at concentration range of 0.1-50%, weight per volume (w/v). The gel formed is within pH 5-7. The composition can be an ethyl cellulose gel, a cream, a waxy cream or other ointment (lotion, cream, or soap). The composition besides the emulsion of NBrT/taurine and stable produced olive oil can contain: beeswax: INCI name: *Cera alba*, to make a waxy cream in concentrations of 1-25% by weight, also, INCI name: *Hypericum perforatum* flower twig extract (INCI name) in concentrations of 1-5% by weight, chamomile extract (INCI name: *Matricaria* Extract) in concentrations 1-5% by weight, bismuth subgalate at concentrations 1-10% by weight, mastic oil at concentrations 0.1-10% and a mixture of preservative agents.

In this invention the biochemical method for producing NBrT/taurine aqueous solutions is as follows: 100 ml of 80 mM NBrT solutions are prepared by making 1600 mM or 20% content by weight of Taurine (AppliChem Panreac, Germany), in sterile double distilled water, 160 mM NaOCl (Sigma Aldrich Germany) in phosphate buffer saline (PBS) pH 7.2, and 160 mM NaBr (Sigma Aldrich Germany) in PBS (Sigma Aldrich Germany) and titrated to pH 10 by NaOH (Sigma Aldrich, Germany). 100 ml of 160 mM NaOCl are mixed with 100 ml of 160 mM NaBr pH 10 to make 200 ml of 80 mM NaOBr. 100 ml of 80 mM NaOBr are mixed gradually with 100 ml of 1600 mM Taurine to make about 80 mM NBrT solution, leaving finally 400 mM of taurine presumably not reacted with NaOBr in the resulted NBrT solution. The produced NBrT concentration in molarity was assessed at measuring the extinction coefficient at a wavelength $\lambda_{max}$=286 nm, where the 10 mM of NBrT equals to the value of extinction with peak 430$M^{-1}$ $cm^{-1}$ (absorbance). S.P.O.O. was prepared using an initial extra virgin olive oil and a filtering procedure through a filter membrane of 100% cellulose, weight 60 g/$m^2$, size of pores 18-20 µm, with a rate of filtration 4 sec/100 ml of water, 01% ash, thickness 20 mm and wet bursting strength: > or equal to 40 kPa as main characteristics. The resulted stable olive oil produced has principal chemical characteristics: K270=0.10, K232=1.69, ΔK=−0.002, acidity=0.30, hyperoxide value=15.7. NBrT/taurine emulsions with S.P.O.O. were prepared by diluting 16 mM of NBrT/80 mM taurine aqueous solutions and mixing with S.P.O.O. in an analogy of 1:1 to SPOO and steered adequately to make an emulsion at temperature not exceeding 30° C.

For better stabilization and avoidance of phase separation of the emulsion NBrT/taurine aqueous solutions and S.P.O.O., xanthan gum may be used preferably at concentrations of 0.8-5% by weight to form stable gel, creams and other ointments. Instead of xanthan gum, ethyl-cellulose at concentrations 0.2-5% may be used. Other ingredients that may be used. to make a cream or other ointment for psoriasis apart from the active emulsion of NBrT/taurine and SPOO are panthenol, bismouth subgalate, extra SPOO, other plant fruit and seed derived oils, for example: mastic, almond and castor oil, *hypericum perforatum* flower twig extract and chamomile extract. Gel, creams or wax ointments should be at pH 5-8.

EXAMPLE 1

8 mM NBrT/40 mM Taurine Gel

A/100 ml of 8 mM NBrT/40 mM taurine gel

Xanthan Gum about 0.8

S.P.O.O.*(from *Olea Europaea* Fruit Oil) 10

80 mM Taurine NBrT & 400 mM Taurine aqueous solutions**10

Water ad 100.0

B/100 ml 0.08 mM NaOBr in phosphate buffered saline

EXAMPLE 2

8 mM NBrT/40 mM Taurine Gel with Excess S.P.O.O.

A/100 ml of 8 mM NBrT/40 mM taurine gel

Xanthan Gum about 0.8

S.P.O.O.*(from *Olea Europaea* Fruit Oil) 20

80 mM NBrT & 400 mM Taurine aqueous solutions**20

Water ad 100.0

B/100 ml 0.08 mM NaOBr in phosphate buffered saline

EXAMPLE 3

8 mM NBrT/40 mM Taurine Modified Waxy Cream/Ointment
A/100 ml of 8 mM NBrT modified waxy cream/ointment
S.P.O.O.*(from *Olea Europaea* Fruit Oil) 10
Mastic oil 1
80 mM NBrT & 400 mM Taurine aqueous solutions**10
Cera alba (beeswax) 5
S.P.O.O. ad 100
B/100 ml 0.08 mM NaOBr in phosphate buffered saline

EXAMPLE 4

8 mM NBrT/40 mM Taurine Waxy Gel.
A/100 ml of 8 mM NBrT/40 mM taurine gel
Xanthan Gum about 0.8
S.P.O.O.*(from *Olea Europaea* Fruit Oil) 10
80 mM NBrT & 400 mM Taurine aqueous solutions**10
Cera alba (beeswax) 3
Water ad 100.0
B/100 ml 0.08 mM NaOBr in phosphate buffered saline

EXAMPLE 5

8 mM NBrT/40 mM Taurine Body Lotion (Milk)
80 mM NBrT & 400 mM Taurine aqueous solutions**10
S.P.O.O.*(from *Olea Europaea* Fruit Oil) 10
Sodium PCA (solution 50% w/w) 1
Emulsifier 3-5
Aloe vera gel 3
Water ad 100.0

EXAMPLE 6

8 mM NBrT/40 mM Taurine Lotion-Solution
80 mM NBrT & 400 mM Taurine aqueous solutions**10
S.P.O.O.*(from *Olea Europaea* Fruit Oil) 10
Propylene glycol 2
Xanthan gum 0.1
Hyaluramin 0.20
Water ad. 100

EXAMPLE 7

10 mM NBrT/50 mM Taurine Medical Device
A/100 ml 10 mM NBrT/50 mM taurine wax ointment
100 mM NBrT & 500 mM Taurine aqueous solutions**10
S.P.O.O.*(from *Olea Europaea* Fruit Oil) 10
Cera alba (beeswax) 5
Mastic Oil 0.1-1
Sunflower Oil 2-5
Bismuth subgalate 3
Sulphur (pure) 0.3-0.5
S.P.O.O. ad 100
B/40×40 cm sterile pure cotton gauze 3-7 g embedded fully in waxy ointment and applied as a medical or surgical dressing. *S.P.O.O.: Stable Produced Olive Oil is the product of GR1008334B patented methodology of refining Olive Oil, preferably Extra Virgin Olive Oil. Olive Oils s an ingredient has the INCI name: *Olea Europaea* Fruit Oil, **Aqueous solutions are a: double distilled sterile water, b: 0.9% NaCl water for injection or c: phosphate buffered saline pH 7.2, as called aqueous solutions, of concentrations 0.1-100% content by weight of NBrT and taurine.

BIBLIOGRAPHY

1. GR1008334(B), Feb. 9, 2013. Stable olive oil production through filtration by cellulose membrane. Inventor: Kyriakopoulos Antonios of Mariou-Panagioti. Intern. Class.: (INT. CL8): C11B, 3/00, B01D 6114.
2. Schon M P, Boehnche W P. Psoriasis, 2005. N Engl J Med 352, 18: 1899-1912.
3. Learn D B, Fried V A, Thomas E L. Taurine and Hypotaurine content of Human leukocytes. 1990. J Leuk. Biology. 48:174-182.
4. Marcinkiewich J, Kontny E. Taurine and inflammatory diseases. Amino Acids. 2014 (1):7-20. doi: 10.1007/s00726-012-1361-4.
5. Marcinkiewicz J. Taurine bromamine: a new therapeutic option in inflammatory skin diseases. Pol Arch Med Wewn. 2009. 119(10):673-6.
6. Olszanechi R, Kurnyta M et al. The role of heme oxygenase-1 in down regulation of $PGE_Z$ production by taurine chloramine and taurine bromamine in 1774.2 macrophages. 2008. Amino Acids. 35: 399-364.
7. EP 1663195 A2 (WO 2004093853A2). Taurine bromamine for inhibiting pathogenic bacteria and fungi growth as well as in microbiocidal composition.
8. Gottardi W, Nagi M. N-chlorotaurine, a natural antiseptic with outstanding tolerability. J Antimicrob Chemother 2010; 65: 399-409.
9. Marcinkiewicz J, Kontny E. Taurine and Inflammatory diseases. Amino acids 2012; 6(1):7-20. doi: 10.1007/s00726-012-1361-4.
10. Comission Regulation (EU) No 432/2012 of 16 May 2012: establishing a list of permitting health claims made on foods, other than those referring to the reduction of disease risk and to children development and health.
11. Logotheti S, Khoury N, Vlahopoulos S A, Skourti E, Papaevangeliou D, Liloglou T, GorgoulisV, Budunoval, Kyriakopoulos A M, Zoumpourlis V. N-bromotaurine surrogates for loss of antiproliferative response and enhances cisplatin efficacy in cancer cells with impaired glucocorticoid receptor. Transl Res. 2016 doi: 10.1016/j.trsl.2016.03.009.
12. Emily R, Greene, S H, Charles N S, and Dipak P. Regulation of Inflammation in Cancer by Eicosanoids. Prostaglandins Other Lipid Mediat. 2011 November; 96(0): 27-36. Published online 2011 Aug. 16. doi: 10.1016/j.prostaglandins. 2011.08.004 PMCID: PMC4051344.
13. Zeldin D C. Epoxygenase pathways of arachidonic acid metabolism. J Biol Chem. 2001. 276(39): 36059-62.
14. Muzzalupo I et al. Lox gene transcript in Olive (*Olea Europaea* L.) Fruits at different stages of maturation: relationship between volatile compounds, environmental factors and technological treatments of Oil Extraction. Scientific World Journal 20012. 532179.
15. Wittkowski K M, Leonardi G, et al. Clinical symptoms of skin, nails, and joints manifest independently in patients with concomitant psoriasis and psoriatic arthritis. Plos One 2011; 6(6) e20279. doi: 10.1371/journal.pone.0020279.
16. Marcinkiewicz J. Taurine bromamine: a new therapeutic option in inflammatory skin diseases. Pot Arch Med Wewn. 2009. 119(10):673-6.
17. Marcinkiewicz J et al. Topical taurine bromamine, a new candidate in the treatment of moderate inflammatory acne vulgaris.—A pilot study. Eur j Dermatol. 2008; 18(4): 433-9,
18. Nagl M et al. Tolerability and efficacy of N-chlorotaurine in comparison with chloramine T for the treatment of chronic leg ulcers with a purulent coating: a randomised phase II study. British J Dermatol. 2003; 149: 590-597.
19. Blake S J, Teng M W L Role of IL17 and IL 22 in autoimmunity and cancer. Actas Dermosifiliogr. 2014; 105(Supl 1):41-50
20. Arvin A N. Varicella Zoster Virus. 1996. Clinic. Microbiol. Rev. 9(3): 361-381
21. Kyriakopoulos A M et al. N-chlorotaurine and N-bromotaurine combination regimen for the cure of valacyclovir-unresponsive Herpes Zoster comorbidity in a Multiple Sclerosis patient.2016. IJMPCR 25476. 7(2): 1-6.

The invention claimed is:

1. A method for treating a condition presenting with hyper-proliferating and/or abnormally proliferating cells in a patient in need thereof, comprising topically applying an emulsion comprising taurine, N-bromotaurine (NBrT) and oil and separately applying a solution of NaOBr topically, and wherein the condition to be treated is selected from the group consisting of psoriasis, cancer, and herpes zoster.

2. The method of claim 1, wherein the ratio of NBrT to taurine is 1:5.

3. The method of claim 1, wherein the NBrT is a ratio of 1:1 with the oil within the emulsion.

4. The method of claim 1, wherein the NaOBr solution has a concentration in a range of 0.0001-99% per weight.

5. The method of claim 1, wherein the NaOBr solution is in phosphate buffered saline and is present in an amount of 0.0001-100% per weight.

6. The method of claim 1, wherein the taurine in the emulsion is a taurine salt.

7. The method of claim 1, wherein the condition to be treated is a psoriasis lesion.

8. The method of claim 7, wherein the psoriasis lesion is plaque, guttate, pustular erythrodermic or inverse psoriasis.

9. The method of claim 1, wherein the condition to be treated is herpes zoster.

10. The method of claim 1, wherein the NBrT and the oil are in a ratio of 1:1, 0.01:100 or 100:0.01 within the emulsion.

11. The method of claim 1, wherein the oil is olive oil.

12. The method of claim 1, wherein the oil is almond oil, castor oil or sunflower oil.

13. The method of claim 1, wherein the oil is vegetable oil.

14. The method of claim 1, wherein the emulsion further comprises at least one of xanthan gum, bismuth subgalate, *hypericum perforatum* flower twig extract, *matricaria* extract, panthenol, fruit oil, beeswax, silk proteins, sodium hyalouronate, elastin, Vitamin A and Vitamin E.

15. The method of claim 1, wherein the emulsion further comprises potassium palm itoyl, hydrolyzed wheat protein, glyceryl stearate or cetearyl alcohol.

16. The method of claim 1, wherein the emulsion includes betamethasone having a content by weight of 0.05-1% and salicylic acid having a content by weight of 1-10%.

17. The method of claim 1, wherein the condition to be treated is cancer.

* * * * *